United States Patent
Blanche et al.

(10) Patent No.: US 11,358,002 B2
(45) Date of Patent: Jun. 14, 2022

(54) METHOD AND APPARATUS FOR NON-THERMAL NAIL, FOOT, AND HAND FUNGUS TREATMENT

(71) Applicant: Raymond R. Blanche, Chatham, NJ (US)

(72) Inventors: Raymond R. Blanche, Chatham, NJ (US); Raymond J. Lanzafame, Rochester, NY (US); David J. Smith, Bedfordshire (GB)

( * ) Notice: Subject to any disclaimer, the term of this patent is extended or adjusted under 35 U.S.C. 154(b) by 415 days.

(21) Appl. No.: 15/387,897

(22) Filed: Dec. 22, 2016

(65) Prior Publication Data

US 2017/0165499 A1    Jun. 15, 2017

Related U.S. Application Data

(63) Continuation-in-part of application No. 14/725,622, filed on May 29, 2015, now Pat. No. 9,555,262.

(60) Provisional application No. 62/004,423, filed on May 29, 2014.

(51) Int. Cl.
*A61N 5/06* (2006.01)
*A61L 2/08* (2006.01)

(52) U.S. Cl.
CPC ............ *A61N 5/0624* (2013.01); *A61L 2/085* (2013.01); *A61N 5/062* (2013.01); *A61N 5/0616* (2013.01); *A61N 2005/063* (2013.01); *A61N 2005/0626* (2013.01); *A61N 2005/0633* (2013.01); *A61N 2005/0643* (2013.01); *A61N 2005/0645* (2013.01); *A61N 2005/0652* (2013.01); *A61N 2005/0659* (2013.01); *A61N 2005/0661* (2013.01)

(58) Field of Classification Search
CPC .................................. A61N 5/06; A61L 2/08
See application file for complete search history.

(56) References Cited

U.S. PATENT DOCUMENTS

| 3,864,847 A | 2/1975 | Friedman |
| 4,646,743 A | 3/1987 | Parris |
| 5,259,380 A | 11/1993 | Mendes et al. |

(Continued)

FOREIGN PATENT DOCUMENTS

| WO | 1999/004628 A1 | 2/1999 |
| WO | 2002/035983 A3 | 5/2002 |

(Continued)

OTHER PUBLICATIONS

International Preliminary Report on Patentability for PCT Application No. PCT/US/2015/033302. dated Nov. 29, 2016. (5 pages).

(Continued)

*Primary Examiner* — Lynsey C Eiseman
(74) *Attorney, Agent, or Firm* — McHale & Slavin, P.A.

(57) ABSTRACT

A method and device for treating an infection of the nail or nail bed and adjacent tissues through non-thermal means is described. The device illuminates an area with light in the near-infrared region of the electromagnetic spectrum. Preferably, light having wavelengths of from about 870 nm to about 930 nm will be used. Further, the device includes light emitting diodes that are capable of emitting ultraviolet light. These lights are intended to provide a sterile environment for a user using the device.

2 Claims, 17 Drawing Sheets

(56) References Cited

U.S. PATENT DOCUMENTS

| | | |
|---|---|---|
| 5,358,503 A | 10/1994 | Bertwell et al. |
| 5,445,608 A | 8/1995 | Chen et al. |
| 5,500,009 A | 3/1996 | Mendes et al. |
| 5,616,140 A | 4/1997 | Prescott |
| 6,090,788 A | 7/2000 | Lurie |
| 6,149,644 A | 11/2000 | Xie |
| 6,743,249 B1 * | 6/2004 | Alden ............... A61N 5/0601 606/1 |
| 7,306,620 B2 | 12/2007 | Cumbie |
| 7,713,294 B2 | 5/2010 | Bornstein |
| 7,793,666 B2 | 9/2010 | Weinfield |
| 8,277,495 B2 | 10/2012 | Demetriou |
| 8,430,104 B2 | 4/2013 | Hennings et al. |
| 8,506,979 B2 | 8/2013 | Bornstein |
| 8,535,359 B2 | 9/2013 | Bornstein |
| 8,696,161 B2 | 4/2014 | Pan et al. |
| 8,814,922 B2 | 8/2014 | Hennings et al. |
| 8,814,924 B2 | 8/2014 | Shanks et al. |
| 2003/0216719 A1 | 11/2003 | Debenedictis et al. |
| 2004/0008523 A1 * | 1/2004 | Butler ............... A61N 5/0613 362/551 |
| 2004/0197280 A1 | 10/2004 | Repka |
| 2005/0256552 A1 * | 11/2005 | White ............... A61N 5/0616 607/88 |
| 2007/0104664 A1 * | 5/2007 | Maltezos ............ A61N 5/0616 424/61 |
| 2008/0058905 A1 * | 3/2008 | Wagner ............. A61N 5/0616 607/88 |
| 2008/0077204 A1 * | 3/2008 | Bornstein ........... A61N 5/0601 607/100 |
| 2008/0082090 A1 | 4/2008 | Manstein |
| 2009/0105790 A1 * | 4/2009 | Bornstein ............ A61L 2/084 607/87 |
| 2009/0143842 A1 * | 6/2009 | Cumbie ............. A61N 5/0624 607/88 |
| 2009/0234270 A1 * | 9/2009 | Loebel ............... A61K 31/125 604/20 |
| 2009/0299441 A1 | 12/2009 | Bornstein |
| 2010/0256551 A1 | 10/2010 | Maltezos et al. |
| 2011/0015549 A1 | 1/2011 | Eckhouse et al. |
| 2011/0020173 A1 * | 1/2011 | Pryor ............... A61L 2/084 422/3 |
| 2011/0152979 A1 * | 6/2011 | Driscoll ............ A61N 5/0616 607/93 |
| 2011/0224759 A1 * | 9/2011 | Shanks ............. A61N 5/0616 607/89 |
| 2011/0295343 A1 | 12/2011 | Bornstein et al. |
| 2012/0016449 A1 | 1/2012 | Mochizuki et al. |
| 2012/0197179 A1 | 8/2012 | Khan et al. |
| 2012/0283622 A1 * | 11/2012 | Nath ............... A61K 31/409 604/20 |
| 2012/0319010 A1 * | 12/2012 | Bornstein ........... A61N 5/062 250/492.1 |
| 2013/0172961 A1 | 7/2013 | Enemaerke |
| 2013/0178919 A1 * | 7/2013 | McNeill ............ A61N 5/0616 607/90 |
| 2013/0211481 A1 | 8/2013 | Ward et al. |
| 2013/0344454 A1 * | 12/2013 | Nath ............... A61N 5/0616 433/29 |
| 2014/0031906 A1 | 1/2014 | Brezinski |
| 2014/0194955 A1 * | 7/2014 | Povolosky .......... A61N 5/0624 607/89 |
| 2014/0200506 A1 | 7/2014 | Zemel et al. |
| 2014/0231677 A1 | 8/2014 | Cheng |
| 2014/0288351 A1 * | 9/2014 | Jones ............... A61N 5/06 600/9 |
| 2014/0288621 A1 * | 9/2014 | Efremkin ........... A61N 5/022 607/89 |
| 2014/0303547 A1 | 10/2014 | Loupis et al. |
| 2014/0303692 A1 * | 10/2014 | Pignatelli .......... A61N 5/0613 607/89 |

FOREIGN PATENT DOCUMENTS

| | | |
|---|---|---|
| WO | 2002062420 | 8/2002 |
| WO | 2003/077996 A2 | 9/2003 |
| WO | 2005/025470 A1 | 3/2005 |
| WO | 2005/046793 A3 | 5/2005 |
| WO | 2007/019305 A3 | 2/2007 |
| WO | 2008/035340 A3 | 3/2008 |
| WO | 2009/059230 A3 | 5/2009 |
| WO | 2009/059270 A1 | 5/2009 |
| WO | 2013005156 | 1/2013 |
| WO | 2013/040542 A1 | 3/2013 |
| WO | 2013/173516 A1 | 11/2013 |
| WO | 2014/018103 A1 | 1/2014 |

OTHER PUBLICATIONS

International Search Report for PCT Application No. PCT/US/2015/033302. dated Aug. 20, 2015. 7 pages.

* cited by examiner

METHOD AND APPARATUS FOR NON-THERMAL NAIL, FOOT, AND HAND FUNGUS TREATMENT

CLAIM OF PRIORITY

This application claims the priority of U.S. application Ser. No. 14/725,622 filed on May 29, 2015 as well as U.S. Application 62/004,423 filed on May 29, 2014, the contents of both of which are herein fully incorporated by reference.

FIELD OF THE INVENTION

The field of the invention and its embodiments relates to a method and apparatus for treating fungal infections of the nail, nail bed, and adjacent tissues through non-thermal mechanisms, namely exposing the areas to light of particular wavelengths for an extended period of time. In particular, the illuminating light will be from the near-infrared region (NIR) of the electromagnetic spectrum as well as light from the ultraviolet (UV) region of the electromagnetic spectrum.

BACKGROUND OF THE INVENTION

The nails of many animals, including humans, are an excellent place for parasites, fungi, and other organisms to thrive. Nails provide an excellent place for these organisms to live because these organisms can be difficult to remove due to the difficulty and pain involved with removing said organisms from these areas. Of the aforementioned organisms, many types of fungi thrive particularly well in these environments. One such fungus is *Trichophyton rubrum* ("*T. rubrum*")—the most common cause of athlete's foot, jock itch, and ringworm.

Further, *T. rubrum* accounts for approximately 80% of cases of onychomycosis, a chronic condition caused by infection of a person's nail and nail bed. Onychomycosis is a fungal infection of the toenails or fingernails that may involve any component of the nail unit, including the matrix, bed, or plate. Onychomycosis can cause pain, discomfort, and disfigurement in the nail and nail bed. Further, it may produce serious physical and occupational limitations, as well as reducing quality of life. In extreme cases, such as infections in patients with diabetes, onychomycosis can result in the loss of a digit.

Today, there are various estimates as to the prevalence of onychomycosis, but in the western world infection rates of up to 18% of the adult population have been cited. For people over age 60, the prevalence is 30% and the prevalence rate of onychomycosis is thought to be even higher in people with diabetes. As these ailments still afflict a large percentage of the world's population, logic dictates that even with modern technology, the field of nail fungus treatment leaves room for improvement.

One method for treating nail fungus is the use of topical agents. Throughout the history of onychomycosis and other nail and nail bed infections, many people have stated a preference for this type of treatment. These techniques do have some positive effect on onychomycosis; however topical agents are unable to penetrate the hyperkeratotic nail plate, which renders them incapable of fully eliminating a serious infection. Treatment using nail avulsion in combination with topical therapy has been somewhat more successful than topical ointment alone, but this approach can be time-consuming, temporarily disabling, and painful. Ciclopirox (Penlac) is an example of a topical agent, which is applied as a liquid or as a lacquer on the nail, for the treatment of mild to moderate onychomycosis caused by *T. rubrum* without involvement of the lunula. Although safe and relatively inexpensive, ciclopirox therapy is seldom effective. Newer topical agents include terbinafine (Lamisil®), itraconazole (Sporanox®), and fluconazole (Diflucan®). Terbinafine and itraconazole therapies are widely accepted while fluconazole is rapidly gaining acceptance in the market as topical and oral agents.

These new medications share characteristics that enhance their effectiveness: prompt penetration of the nail and nail bed, persistence in the nail for months after discontinuation of therapy and generally good safety profiles. Although published studies indicate good efficacy for these treatments, particularly with the oral forms of these agents when used to treat onychomycosis, the length of the treatments is equal to the time it takes for the nail to grow out, which is typically 4-9 months. Further, the associated side effects of these new drugs make them very unattractive for many potential users.

These pharmaceutical compounds exert their effect by inhibiting and halting the growth of the causative fungal organisms. While this method has also proved effective, ingesting these pharmaceutical compounds has proven to be toxic to a user's liver, and frequently results in expensive and burdensome monitoring of a patient's blood chemistry.

Current systems that are used to treat such nail fungi often employ either Class 3R or Class 4R lasers. One such laser is a Nd:YAG laser which produces burst of short pulses of laser light at 1064 nm. These bursts of light raise the temperature of the fungal hyphae, through selective absorption, the main mode of vegetative growth for fungi. If a temperature of 65° C. (149° F.) is maintained for 7 seconds, this is sufficient to denature the proteins of the fungi and cause permanent damage to the fungi. The light absorption is selective, which means that the temperature of the nail bed does not exceed 45° C. (113° F.) during the treatment and causes no damage to healthy tissue. These systems are highly effective at removing the fungi, however, they often cause pain to the receiver of the treatment. This pain is caused by the body of the receiver of treatment absorbing a large percentage of the laser's light, resulting in an increase in temperature which leads to pain. This means that whenever a patient wants to get their nail fungus removed via laser, they will have to experience great pain.

Thus, there is a need for a method and apparatus for an effective treatment of nail fungi that does not cause the user pain, does not subject the user to any potential harm, and does not result in the user incurring any undue expense.

There have been developments in anti-fungal treatments using Low Level Laser Therapy ("LLLT"). The attraction of this type of device is the inherent safety of the wavelengths in the near infrared and the low levels of energy and consequently lower temperatures used in the treatment. In addition, unlike Photodynamic Therapy (PDT), there is no requirement for a photosensitising agent. PDT has been proposed by many as a possible treatment for onychomycosis, but getting the photosensitising agent through the nail into the nail bed poses a significant challenge. The process of photodamage to the fungal hyphae using LLLT is a very complex one and not entirely understood, although there is clinical evidence to support its use. In a 1999 study by Neuman, it was discovered that two peaks at 870 nm and 930 nm in caused significant photodamage to *E. coli*. See Neuman et al., *Characterization of Photodamage* to *Escherichia coli* in *Optical Traps*, Biophysical Journal 77, November 1999.

Since then, the most notable development in this field is the Noveon laser produced by Nomir Technologies, Incorporated. The Noveon is a laser diode system which operates at two wavelengths—870 nm and 930 nm—both of which have been shown to demonstrate anti-fungal properties. Several studies have been carried out, the most significant being by Landsman. There, a 180-day study of the effects of theses wavelengths on the treatment of onychomycosis. See Landsman, et al. *Treatment of Mild, Moderate, and Severe Onychomycosis Using* 870- *and* 930-*nm Light Exposure*, Journal of the American Podiatric Medical Association, 100(3), May/June 2010. A subsequent 270-day follow up was also carried out. These studies demonstrated the selectiveness of these wavelengths to negatively affect only fungi and bacteria, not mammalian cells. The claimed embodiments are directed towards a method and apparatus capable of exploiting these phenomena to provide a safe and effective way to cure onychomycosis.

Review of Related Technology:

United States Patent Application Publication Number 2012/0283622 pertains to a dermatological treatment device primarily suitable for treating nail fungus. This publication discloses the use of a photochemically active substance, effectively controlling the fungus by irradiating it with light at a wavelength that has no ancillary effects on the patient's health. It is possible to use either a gas discharge lamp or light emitting diodes as an appropriate light source for the claimed method and apparatus. Preferably, a transparent shoe-shaped optical shielding housing that absorbs short-wave light is used.

U.S. Pat. No. 7,306,620 pertains to a method for the prevention and treatment of microbial infections that occur on, or just below, the skin and nails of a person. The treatment consists of irradiating an area of the skin and nails for a period of time long enough to kill the organisms causing the infection. Additionally, some optional features increase the safety of the treatment. These options achieve this by shielding non-infected areas from irradiation, and including a cover to prevent damage to sight which may result from viewing the electromagnetic radiation.

United States Patent Application Publication Number 2005/0256552 pertains to a battery-powered toenail fungus eradicator that can be comfortably worn while sleeping. Alternatively, this device can be worn continuously.

U.S. Pat. No. 5,616,140 pertains to a method and apparatus for therapeutic laser treatment. The apparatus comprises a portable, battery-operated, laser bandage having a plurality of hyper-red light emitting diodes. This laser bandage may be worn by a patient and applied to a specific treatment area. The patient may wear the device for up to a week in between visits to their prescribing physician. At the end of the prescribed treatment length, the physician may re-program the device for a different treatment regimen, if desired. Alternatively, the physician may substitute the battery contained in the apparatus and continue said prescribed treatment regimen. The disclosed device is small enough to be worn under clothes so that it will not interfere with the patient's normal activities.

International Application WO2003/077996, published under the Patent Cooperation Treaty, pertains to a device and method for treatment of the external surfaces of a body by utilizing a light-emitting container. The device is comprised of a patch or bandage, applied on or adjacent to a specific external surface of a human or animal body part. This device then delivers light of varying intensity, wavelengths, duration. The exposure to this varying light is intended to treat fungi, among other things.

Review of Present Invention in Light of the Prior Art:

None of the art described above addresses all of the issues that the present invention does. The claimed invention includes a power source, at least one light emitting diode capable of generating light with wavelengths between about 800 nm and 980 nm, configurable printable circuit boards, and a chamber with a digit-receiving area. Studies have shown that flooding the treatment area with light having wavelengths at or about 870 nm and about 930 nm provides an adequate means for treatment. Optionally, the chamber can be equipped with an interchangeable bottom plate, and at least one additional light source capable of generating ultraviolet light.

The present invention provides for more complete exposure of the treatment area and adjacent tissues with NIR light than has previously been contemplated. The present invention uses both light emitting diodes capable of producing NIR and ultraviolet light. No other device in the prior art contains both of these features. The combination of these features allows for multiple users to use the same device shortly after each other without compromising patient safety and while maintaining sanitary conditions within the chamber of the invention.

When compared with other devices of the same nature, the present invention provides a chamber containing an area capable of receiving a user's digits, allowing the area to be treated to be fully exposed to the treating light emitted by both an array of light emitting diodes and the ultraviolet light emitting diode(s). For instance, if a user wanted to treat an infection of *T. rubrum*, the fungus most often responsible for athlete's foot, the user would place the foot into the digit receiving area of the invention. This user's foot would then be exposed to light from the array of light emitting diodes ranging from about 840 nm to about 980 nm as well as a dose of ultraviolet light, optimally at about 383 nm, which is used to primarily sterilize the device between treatments. Research from the University of Tokushima in Japan shows the sterilisation effects in both air and water at wavelengths of 365 nm and 385 nm. This exposure will result in killing the fungus without causing the user to feel any heat or discomfort. The fact that the user experiences no discomfort is an improvement over the prior art which generated an overabundance of heat in the user.

Another feature that differentiates the present invention is the configuration of the light emitting diodes. In a preferred embodiment, the light emitting diodes are arranged an array on the top of the chamber as well as embedded in posts to be inserted in between a user's digits. The posts are adjustable so that the distance between these posts can be appropriately configured to optimally treat the user's digit. As the posts are adjusted, the light emitting diodes should be able to fully illuminate the treatment area of the user. These adjustable columns are a significant departure from the prior art.

Thus, the present invention solves a number of issues that other devices in the field do not and as such it is novel and unique to the field.

SUMMARY OF THE INVENTION

The claimed invention is a method and apparatus for treating and preventing fungi from infecting a nail or nail bed through non-thermal means. The apparatus comprises: a power source, at least one light emitting diode operatively connected to the power source, a chamber, having an inner surface, outer surface, and a digit-receiving area, wherein said digit-receiving area optionally contains a pitted grid on its bottom surface. The light emitting diode(s) emit(s) light with a wavelength that ranges between about 840 nm and about 980 nm, and at least one of said light emitting diodes is affixed to the chamber's inner surface, in an orientation that allows the light emitting diode to illuminate the digit-receiving area when desired. Optimally, wavelengths of about 870 nm and about 930 nm will be emitted. The apparatus may also be optionally configured to have a hinged top comprising the top of the chamber.

Further, a method for disease prevention and treatment, comprising first placing at least one digit inside an chamber, wherein said chamber has an inner surface, outer surface, and a digit-receiving area wherein said chamber has at least two light emitting diodes wherein the second light emitting diode is capable of generating light with a wavelength of about 383 nm is affixed to the inner surface of said chamber, wherein said digit-receiving area has a top and bottom surface; then powering the light emitting diodes so that the light at wavelengths of about 870 nm and about 930 nm is generated; then allowing the digit to remain in the chamber for a first predetermined amount of time; and finally repeating the above steps for a predetermined amount of time.

Moreover, the claimed invention contemplates an embodiment where a sterilization device comprises: a power source; at least one light emitting diode operatively connected to said power source, wherein said light emitting diodes emit light at wavelengths between about 870 nm and about 930 nm; a spine, having a, frontal and distal end; a plurality of fingers, having a top and bottom surface and a frontal and distal end, wherein the finger's distal end is hingedly attached to said spine, wherein the at least one light emitting diode is attached to said finger; and a chamber having a top and bottom surface, and a digit-receiving area, wherein said digit-receiving area has at least a bottom surface, wherein at least one light emitting diode is affixed to said chamber's inner surface, in an orientation that allows the light emitting diode to illuminate the digit-receiving area when desired.

During the treatment, it is possible for the unit to become contaminated with fungus and therefore, if the unit is shared with others, cross infection between users could occur, and/or the user could inadvertently recontaminate previously treated digits. It has been demonstrated that the treatment using the combination of the two wavelengths has an inhibitory effect on the targeted fungi, which would suggest that any residual fungi left in the device after the treatment could be affected by running the treatment cycle a second time (a 'clean' cycle) without the user's digits being present.

It is an object of the invention to provide a treatment apparatus that allows for treatment of fungus located on a user's nail or nail bed.

It is an object of the invention to provide a treatment apparatus that allows for the treatment of fungus located on a user's digit.

It is an object of the invention to provide a treatment apparatus that allows for the removal of fungi from a user's shoe.

It is an object of the invention to provide a treatment apparatus that allows for the treatment of fungus located on a user's digit without generating excessive heat to the point where the user is caused pain.

It is an object of the invention to provide a treatment apparatus that allows for the treatment of fungus located on a user's digit while being adjustable so that the apparatus is optimized for a particular user.

It is an object of the invention to provide a treatment apparatus that also uses ultraviolet light emitting diodes to sterilize the chamber between users.

It is an object of the invention to provide a method utilizing the aforementioned treatment apparatus.

DESCRIPTION OF THE PREFERRED EMBODIMENTS

Figure 1:
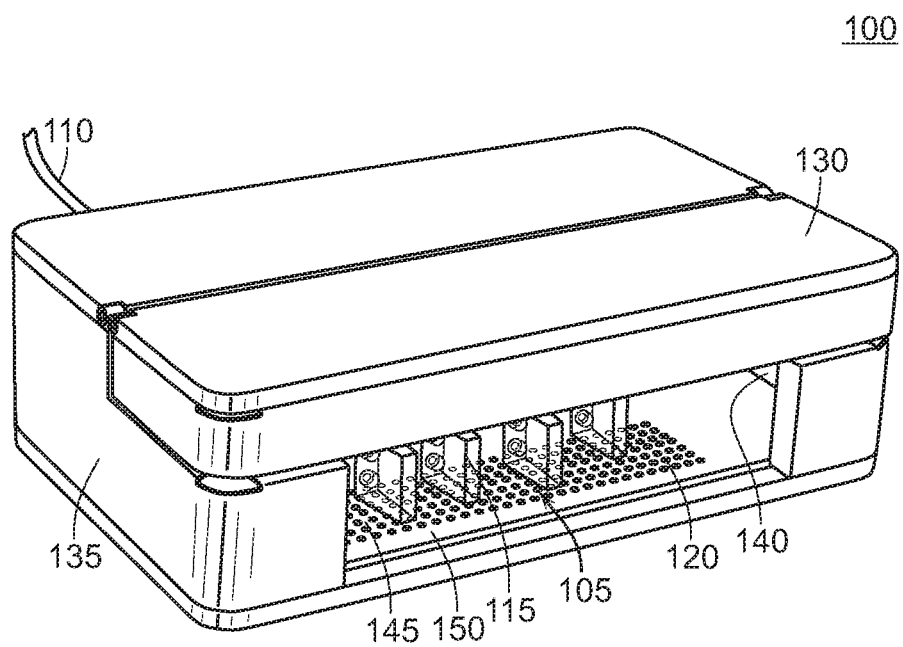
FIG. 1 is a front-perspective view of one embodiment of the apparatus of the claimed invention.

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

Generally, the embodiments described herein may operate on a principle of a generation of a reactive oxygen species (ROS) or chemically reactive species containing oxygen within or by the tissue of the host or user. The reactive oxygen species generated may be at least one of hydrogen peroxide, hydroxyl radical, hydroxyl ion, hypochlorite ion, hypochlorous acid, nitric oxide, peroxyl radical, peroxynitrite anion, singlet oxygen, or superoxide anion, or the like or a combination thereof.

Certain fungi have been shown to be susceptible to light therapies. For example, light normally inhibits the mating cycle of c. neoformans. Further, applying light of certain wavelengths to tissues, as described herein, may cause a generation of an oxidative burst of reactive species. This process may be enhanced by utilizing the light therapy in combination with another medication such as a photosensitive medication. Light/tissue interactions with other endogenous chromophores present in the user or host may also result in production of ROS species amongst other endogenous molecules as described herein. The creation of these ROS FIG. 1 shows the overall arrangement of one embodiment of the claimed invention. The device 100 has an inner surface 140, an outer surface 135, and is operatively connected to a power source 110. The device includes an illumination chamber 105. In this embodiment, the top of the illumination chamber 105 is comprised of a hinged lid 130. Hinged lid 130 can be lifted up to allow the device 100 to be serviced and the posts 115 to be adjusted. Power source 110, among other things, operates the light emitting diodes contained inside posts 115.

Figure 2:
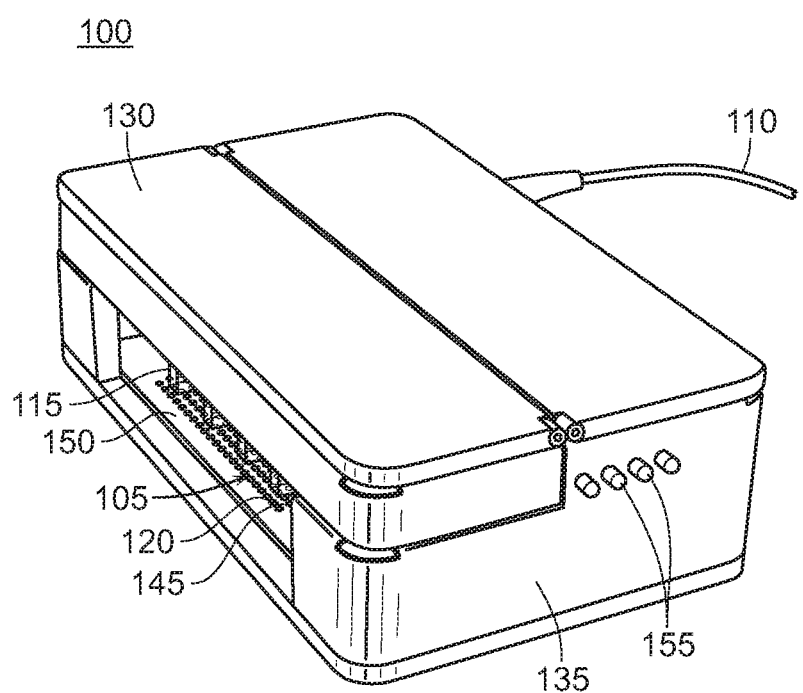
FIG. 2 is a right-perspective view of an embodiment of the apparatus of the claimed invention.

FIG. 2 shows the embodiment of the claimed invention shown in FIG. 1 with the status light emitting diodes 155 being attached to outer surface 135. These status light emitting diodes 155 can indicate at least whether the device is powered on, in a cleaning cycle, treatment cycle, or ready for a treatment. The specific indication given by the status light emitting diodes 155 can be configured based on a given manufacturer's preference.

Figure 3:
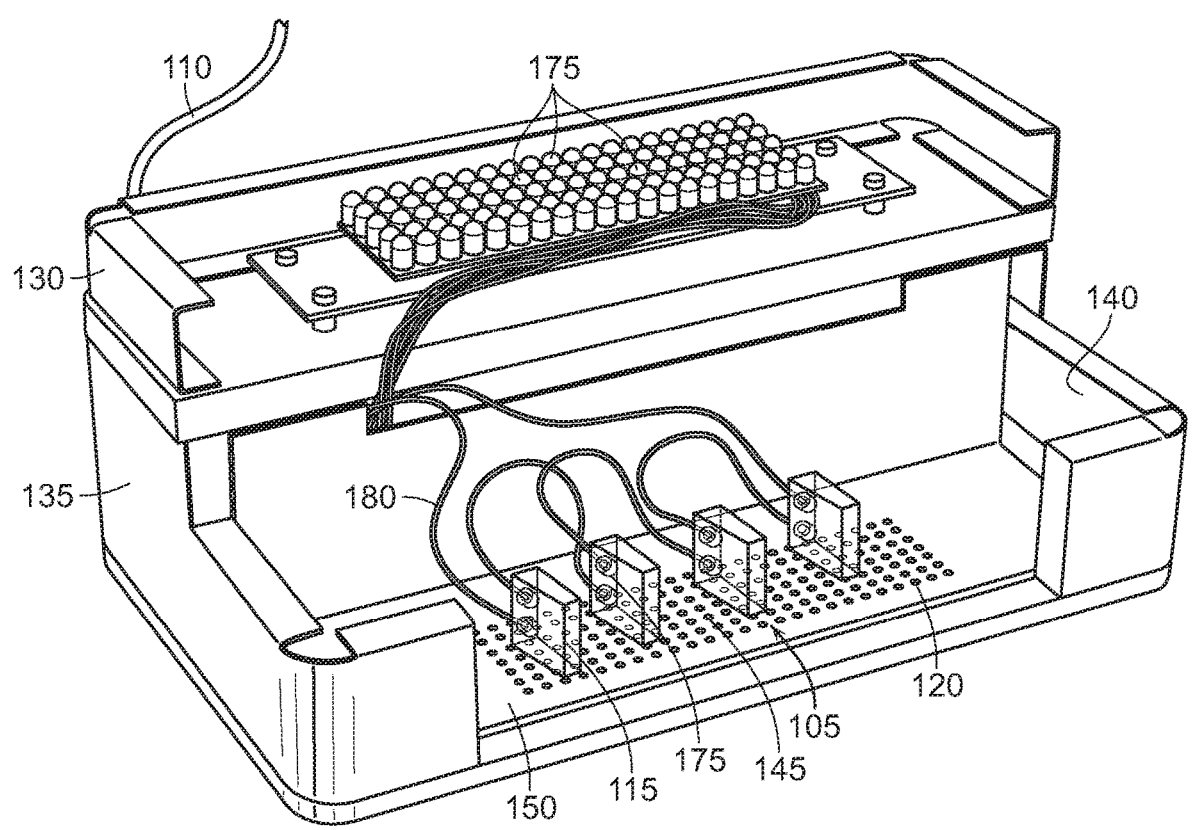
FIG. 3 is a front-perspective view of an embodiment of the apparatus of the claimed invention with a hinged lid in the open position.

FIG. 3 shows another view of an embodiment of the present invention. In this embodiment, the hinged top 130 is in the open position, exposing the inside of the illumination chamber 105. This view shows the wires 180 used to operatively connect the light emitting diodes 175 to the power source 110. Note that while this embodiment connects the posts 115 to the power source 100 via wires 180, other embodiments exist where posts 115 are connected wirelessly to the electrical systems of the device 100. This view also shows the digit receiving area 145, as well as the pitted grid 120 that comprises the bottom of the digit receiving area 145. The interchangeable plate 150 can also be seen from this angle. The interchangeable plate comprises the entire bottom of the illumination chamber 105. This plate may be swapped out after a user has finished a treatment cycle. This can aid in the sterilization process of the device 100 or aid in the replacement of a damaged interchangeable plate 150.

In a preferred embodiment, the light emitting diodes 175 comprise pairs of light emitting diodes with peak wavelengths of about 870 nm and about 930 nm, viewing angles of ±10°, average powers of about 50 mW and about 35 mW, and peak powers of about 500 mW and about 350 mW, respectively for each of the wavelengths. The normal continuous operating current for these devices is approximately 100 mA, which delivers the average power output. In order to achieve the peak power output, it is necessary to overdrive the current to approximately 10 times the continuous level, which would be about 1.0 A peak. In order to stay within the safe operating area of the devices, this peak current can only be maintained for a maximum pulse width of 100 µs and the average power dissipation of the device must not be exceeded. In this embodiment, after considering the energy dissipation and the average size of the digits to be treated, the diameter of the light emitting diodes should be approximately 5.0 mm and the light emitting diodes are to be placed about 25.4 mm from the surface of the digit to be treated.

In another preferred embodiment, the array of light emitting diodes 175 should be about 120 mm by about 34.5 mm. This array conveniently forms twenty rows of six light emitting diodes 175 or perhaps more usefully, ten double rows of six. While not explicitly shown in FIG. 3, the device 100 may have light emitting diodes 175 capable of emitting UV light incorporated into the array of light emitting diodes 175.

Figure 4:
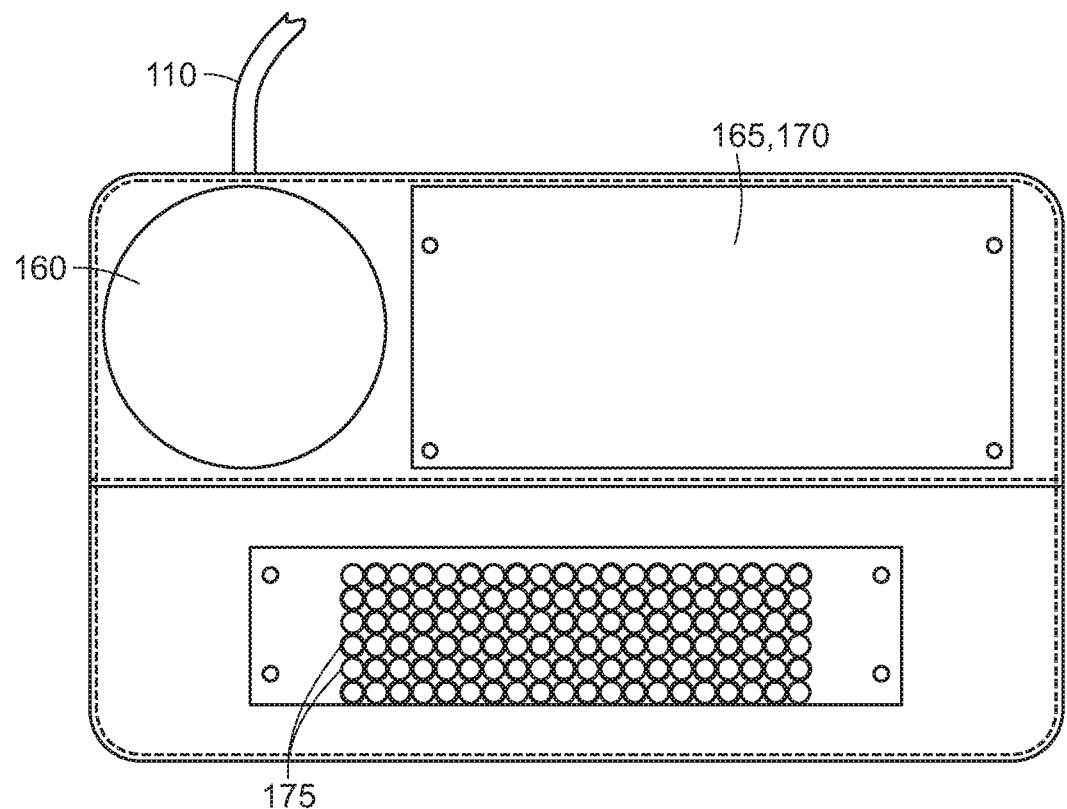
FIG. 4 is a top view of a cross section of an embodiment of the apparatus of the claimed invention, highlighting the internal electrical components of the apparatus.
Figure 6:
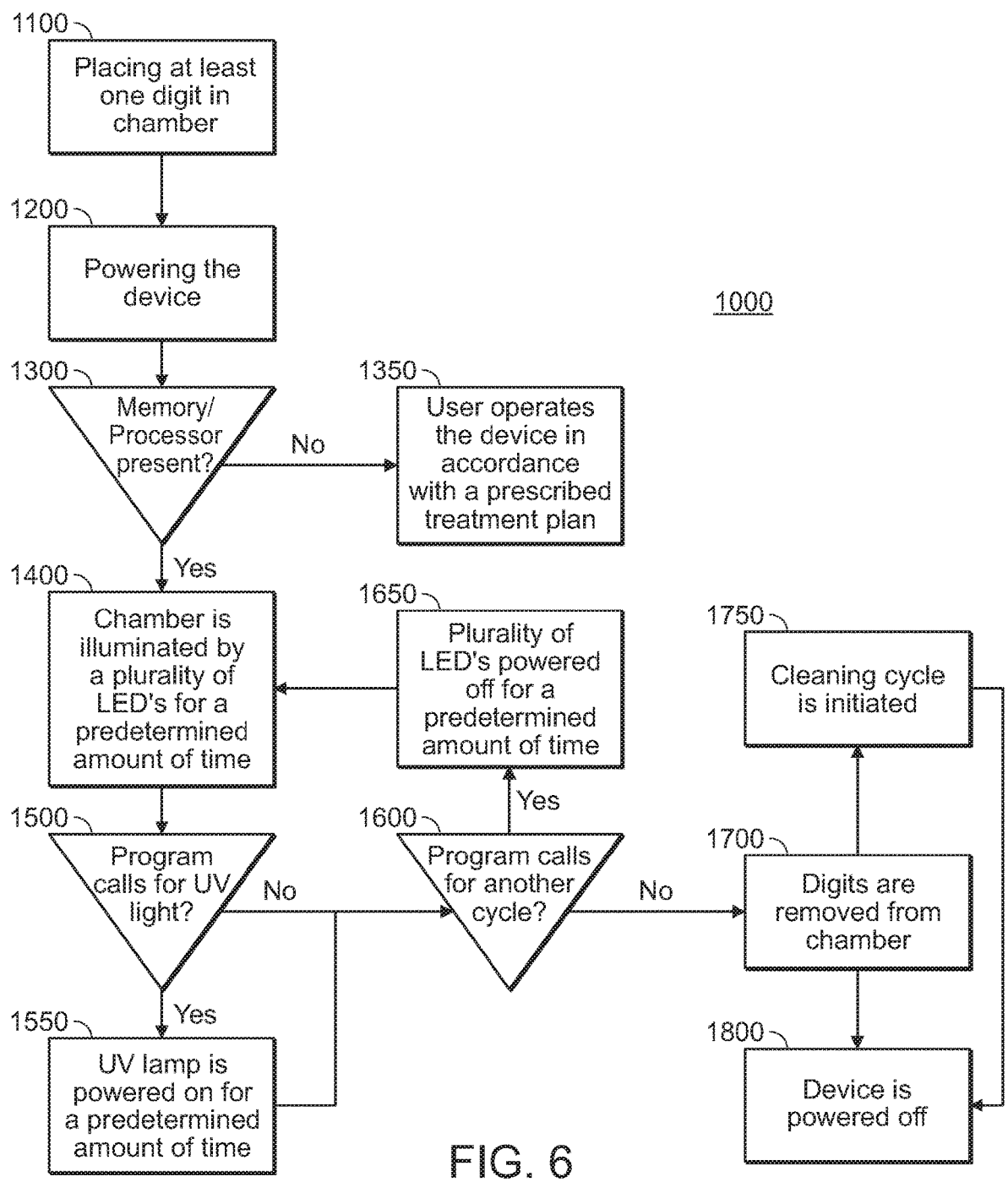
FIG. 6 is a flow-chart showing the steps of an embodiment of the method of the claimed invention.

FIG. 4 illustrates the composition of one embodiment of the present invention. This is embodiment part of the power supply 110, a transformer 160 is shown. Further, two printable circuit boards 165 and 170 are illustrated by FIG. 6. These printable circuit boards 165 and 170 allow the device 100 to be controlled by a user. Printable circuit boards 165 and 170 can also be configured to include a memory and a processor capable of storing information on how to perform predetermined treatment cycles. For example, if a user is to receive two cycles of 10 minutes of irradiation at about 870 nm and about 930 nm, this memory and processor would contain the steps needed to execute such a cycle. This would allow a user to merely push one button to initiate their prescribed treatment cycle.

In a preferred embodiment, the printable circuit boards comprise a power supply board and a timer board. This would allow the apparatus of the claimed invention to be powered off automatically after a predetermined amount of time. The power supply board will provide a regulated 12V of direct current voltage for control circuitry and an unregulated 42V of direct current voltage supply for the power to the chains of light emitting diodes, which will be regulated as shown previously with constant current sources. Further, there will be a separate timer board to provide the countdown timer and the pulsing on and off of the light emitting diodes chains at a pulse width of 100 µs and frequency of approximately 615 Hz. With this system, the light emitting diodes 175 current can be set with an analogue voltage which can be gated on and off to give the pulse regulation. The overall direct current supply would no longer need tight voltage regulation, reducing complexity and cost, as the current is set to a constant level by the control circuitry at the bottom of each chain, as shown below.

In yet another preferred embodiment, the transformer 160 has a twin primary windings so that the transformer 160 can be configured for 115V input (USA) and 230V input (Europe). Here, the first printed circuit board 165 and the second printed circuit board 175 have the same footprint and stack on top of one another. In another embodiment, printed circuit board for the control of the light emitting diodes 175 is attached to the underside of hinged lid 130, which has a double hinge arrangement to enable it to fully open and lay flat on the rear section of the top cover, giving full access to the treatment area.

In yet another embodiment, the hinged cover for the treatment area is interlocked with a micro-switch which prevents the device from operating while the cover is open. Apart from the possibility of UV exposure, the emission from the NIR light emitting diodes 175 is outside the visible spectrum, but the lens of the eye will still transmit and focus this wavelength onto the retina which could cause damage. As this is outside the response of the eye, there is no response of the iris to the intensity of the light output and thus there is no blink response, hence the need to prevent operation in this state.

Figure 5:
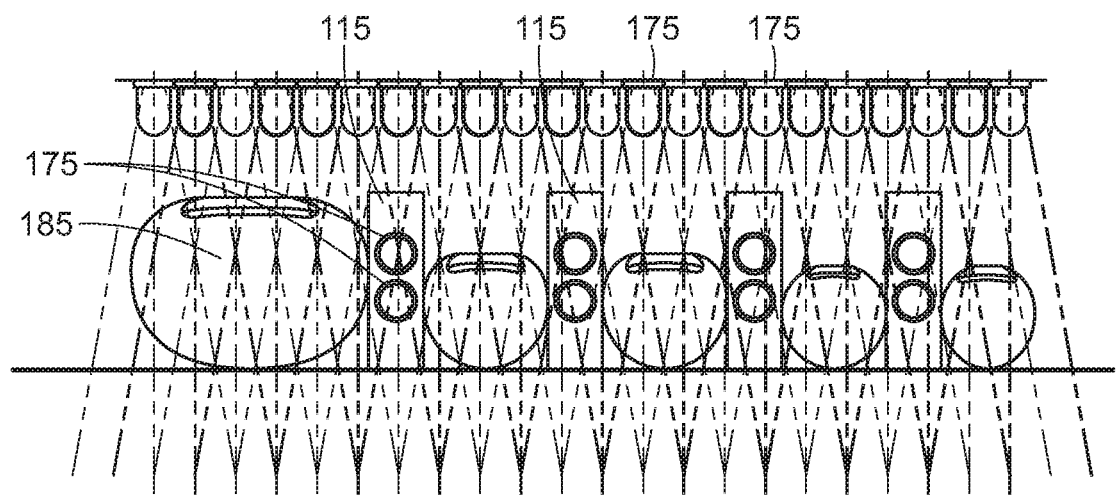
FIG. 5 is a front view of an embodiment of the apparatus of the claimed invention while in use by a human user.

FIG. 5 shows a representation of the present invention while in use. The light emitting diodes 175 and the posts 115 are emitting light at least one predetermined wavelength. These light emitting diodes 175 and posts 115 are capable of emitting light with a wavelength from about 350 nm to about 1000 nm. In a preferred embodiment, the light emitting diodes 175 and posts 115 emit light at about 383 nm, about 870 nm, and about 930 nm. Different light emitting diodes within the plurality of light emitting diodes 175 can be optimized to emit light at different wavelengths. The posts 115 are capable of being adjusted to properly hold and contain a user's digits 185. Note that, it is predicted that the posts 115 will provide more complete exposure of the treatment area which will result in a quicker, more robust treatment of onychomycosis. In a preferred embodiment, the light emitting diodes 175 are both through-hole style with a diameter of 5 mm. In another preferred embodiment, the posts 115 are comprised of a cylinder 8 mm in diameter. Thus, if a 2 mm diameter stainless steel pin is used in the base of the post 115, the pitted grid 120 can be used to position the posts 115 and hold them upright. This arrangement would provide for complete illumination of the toenails and inter-digital spaces of the user.

FIG. 6 illustrates the steps of one of the embodiments of the method of using the claimed apparatus. This method begins with step 1100, where the user places at least one of their digits into the apparatus of the claimed invention.

In step 1200, the device is powered on. Step 1300 comprises a question with potentially divergent results.

Step 1300 considers if the apparatus of the claimed invention contains a memory and a processor. If so, the apparatus of the claimed invention will begin to execute the contents of its memory and proceed to step 1400. If not, this embodiment of the disclosed method requires the user to manually control the light emitting diodes and the posts to comply with a prescribed treatment program.

In step 1400, the light emitting diodes and the posts illuminate the illumination chamber at least with light having wavelengths of about 383 nm, 870 nm, and 930 nm.

In step 1500, the processor checks the memory to see if the prescribed treatment program mandates irradiating the user's digits with ultraviolet light. In a preferred embodiment, this light has a wavelength of about 383 nm. If the prescribed treatment program does call for irradiating the user's digit, step 1550 will be executed and the digit will be irradiated.

If the prescribed program does not call for ultraviolet light, the method will proceed to step 1600. There, the method checks the memory to determine if the treatment cycle needs to be repeated. If so, the light emitting diodes and the posts will turn off for a predetermined amount of time in step 1650, and then proceed back to step 1400. If the treatment cycle is not to be repeated, the embodiment progresses to step 1700.

In step 1700 the user's digits will be removed from the illumination chamber, and then the method determines whether a cleaning cycle should be initiated. If so the embodiment proceeds to step 1750 and a cleaning cycle is started. If not, the method proceeds to step 1800 and the device is powered off. In one embodiment of the method, a treatment cycle will last for fifteen minutes.

Figure 7:
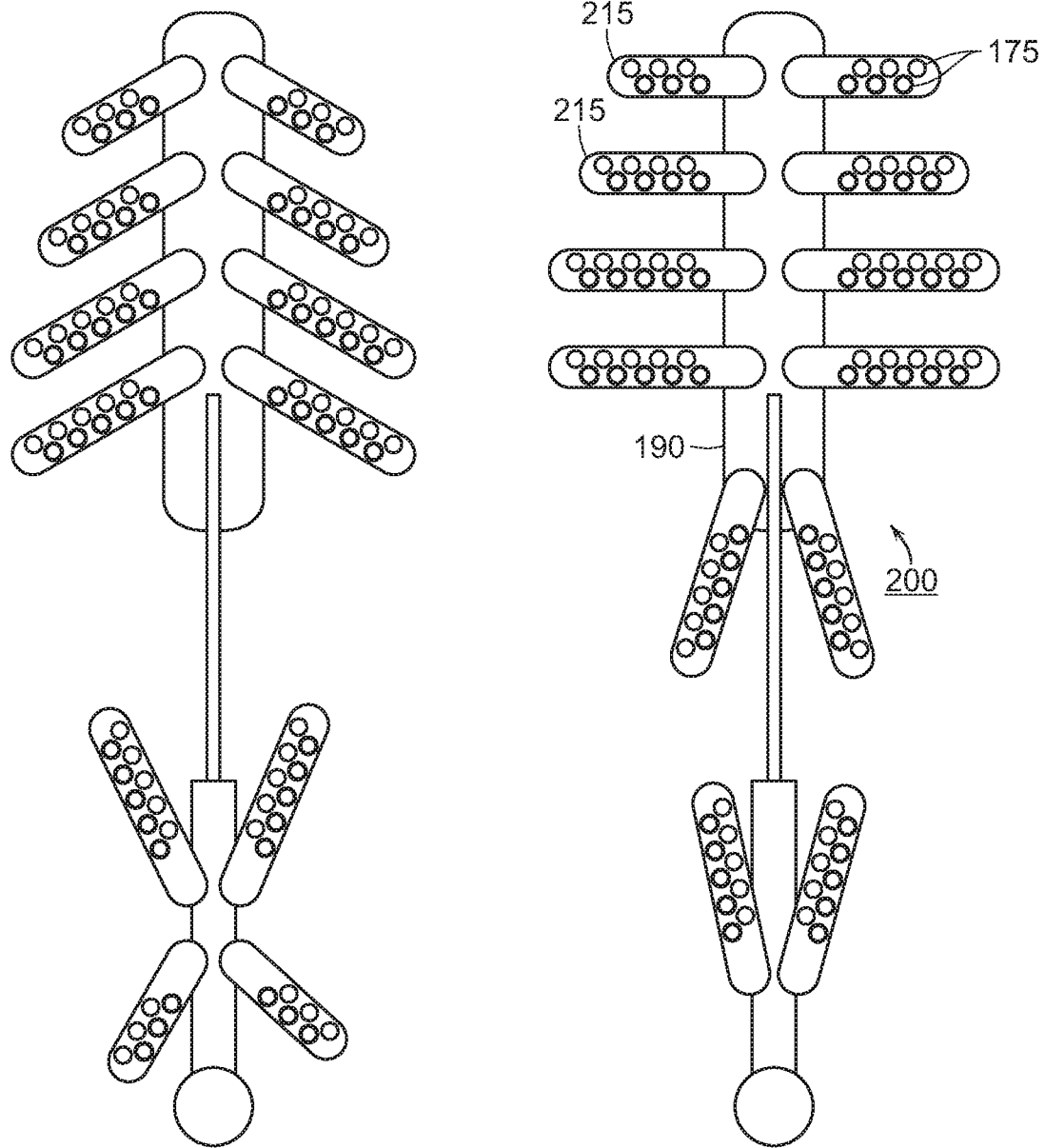
FIG. 7 is a top view of yet another embodiment of the claimed invention.
Figure 8:
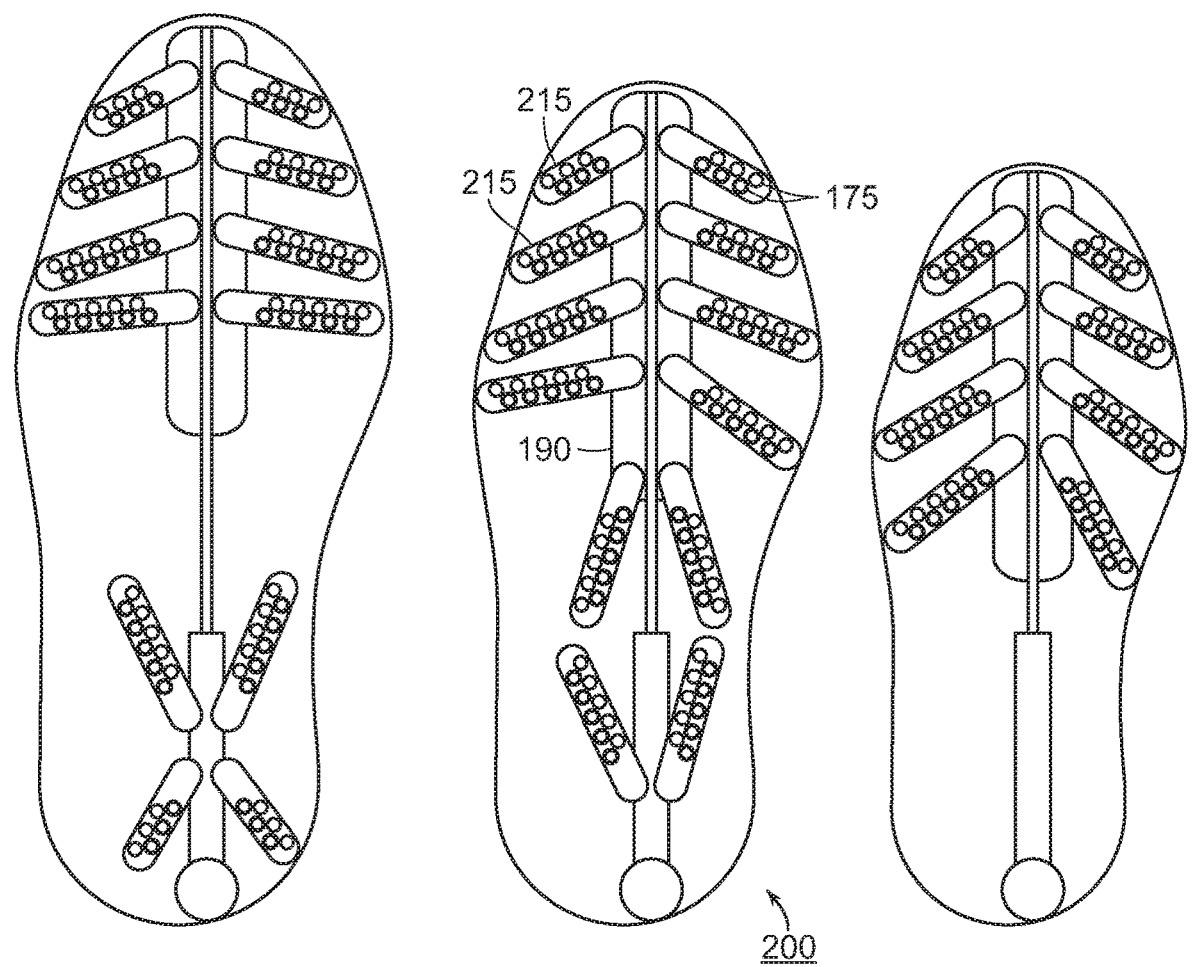
FIG. 8 is a top view of an embodiment of the invention showing how the embodiment contorts to allow for sterilization of a user's shoe.

FIG. 7 and FIG. 8 show an embodiment of the apparatus specially optimized to sterilize a user's shoe by removing any fungi from said user's shoe. It is important to note that the mechanism of light emitting diodes 175 is the same here as it is in earlier mentioned embodiments of apparatus of the claimed invention. An important difference is that in the sterilization device 200, instead of the light emitting diodes 175 being in a static array, the light emitting diodes 175 are located on the fingers 215 of the embodiment that extend from spine 190. In another preferred embodiment, each finger 215 consists of a printed circuit board potted in resin with a 90° torsion spring about the pivot point with spine 190 to give a resting position perpendicular to the central spine. This mechanism allows the fingers to extent to the outer limits of the shoe, as depicted in FIG. 8.

In each finger there are six (3 pairs) NIR light emitting diodes 175 facing both upwards and downwards and between each pair, there is one UV light emitting diode 175 centrally mounted. The upper and lower light emitting diodes will need to be staggered to enable them to be mounted to the printable circuit board. In order to accommodate the shape of a typical shoe, there are preferably at least three different length of fingers 215, mirrored on either side of the central spine 190. With the front, or foot portion 225, of the shoe irradiated in this way, the heel portion 220 of the shoe will also require exposure.

In FIG. 7, there are fingers 215 located in a heel portion 220 of the sterilization device 200. The two configurations shown demonstrate the manner in which the fingers 215 may be arranged in order to provide adequate lighting coverage to the article of footwear. The two configurations are intended to be illustrative of possible configurations and those skilled in the art will recognize many variations of the placement of the fingers 215 exist.

There may be multiple fingers 215 employing a torsion spring about a pivot point to "fan out" over the heel portion 220. Additionally, the fingers 215 may be directed from both the heel portion 220 and the foot portion 225 towards the heel portion 220 thereby providing lighted coverage for the heel portion 220. The fingers 215, as shown in FIG. 8, can be arranged to provide complete coverage for an article of footwear, or may only be present on the foot portion 225. If present only on the foot portion 225 the sterilization device may further employ a lighted heel cup (see FIG. 9). However, the heel cup as described may be used in conjunction with the fingers 215 on the heel portion 220 as well.

Figure 9:
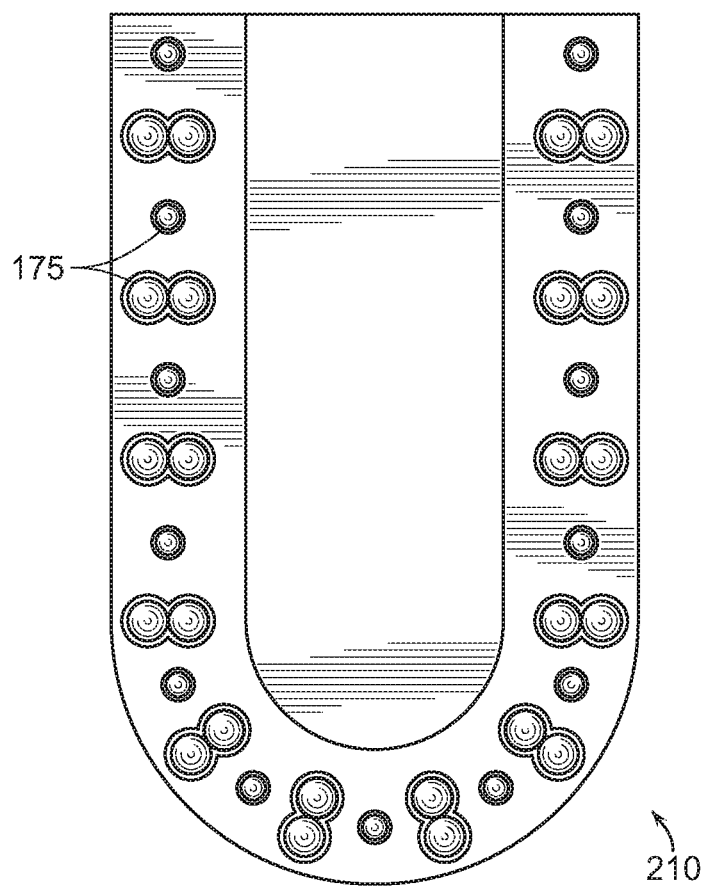
FIG. 9 is a top view of another embodiment for exposing the heel of a shoe to near-IR and UV light.

Referring now to FIG. 9, there is the heel cup element of a particular embodiment of the device intended to clean and sterilize the heel portion of a user's shoe. As with the fingers 215 (see FIG. 8), a printable circuit board potted in resin is contained in a heel cup like structure. This printable circuit board is mounted on a spring loaded shaft to hold it against the rear of the shoe.

Figure 10:
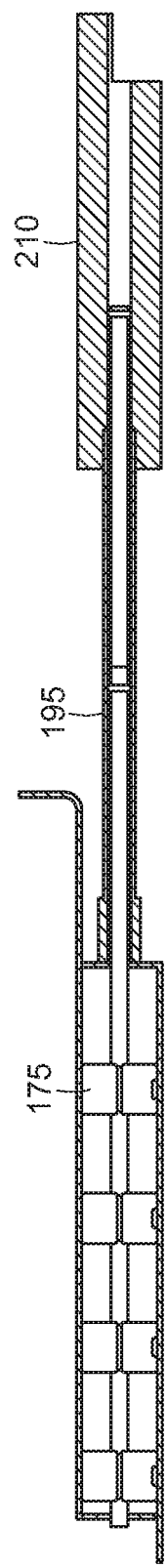
FIG. 10 is a side view of a fully extended embodiment of the claimed invention.
Figure 11:
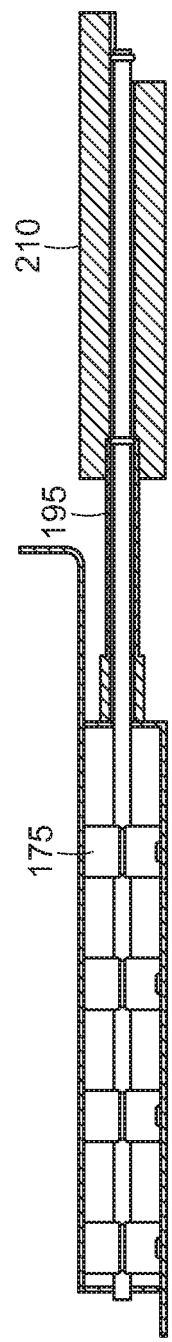
FIG. 11 is a side view of an embodiment of the claimed invention in a compressed position.

FIG. 10 and FIG. 11 show the operation of the central shaft 195. This central shaft 195 provides two functions: the adjustment of the fingers, and the support and positioning of the heel plate. In one embodiment, in order to accommodate the movement required to bring the fingers close into the spine 190, the central shaft 195 needs to move forward by approximately 5 mm.

For the embodiment shown in FIG. 10 and FIG. 11, the fingers are mounted between two thin steel plates. The lower of the two is slightly extended at the front end to provide a front stop for the device. Two vertical plates, front and rear set the height of the device and allow for the position of the central shaft 195. The upper plate has a 90° bend to act as a holding point when the device is compressed for removal. It will require preferably two compression springs in order to accommodate the adjustment required. A spacer and spring guide butts up against the rear vertical plate and a snap ring on the rear of the central shaft 195 prevents the heel plate from becoming detached under the spring pressure. The heel plate 210 can slide forward on the central shaft 195 and will compress the springs, which will hold the heel plate 210 against the rear of the shoe. At this stage, the central shaft 195 will have no impact on the position of the fingers 215 within the shoe, which will find their own position.

When the device is removed, the heel plate 210 is pushed further forwards and will push against a second snap ring on the central shaft 195. This will push the central shaft 195 forwards and angle the fingers into the spine 190 for ease of removal.

Figure 12A:
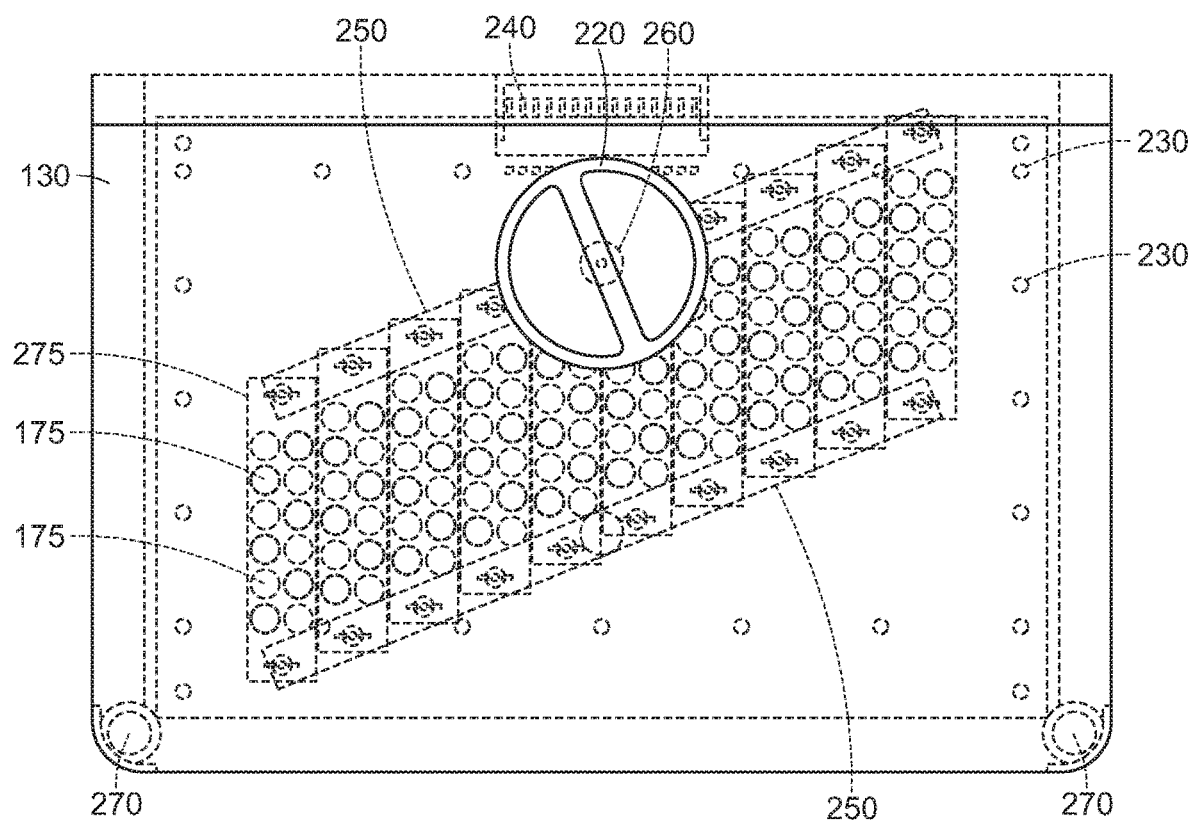
FIG. 12A is a plan view of another embodiment of the present invention configured to receive a left oriented digit or group of digits.
Figure 12B:
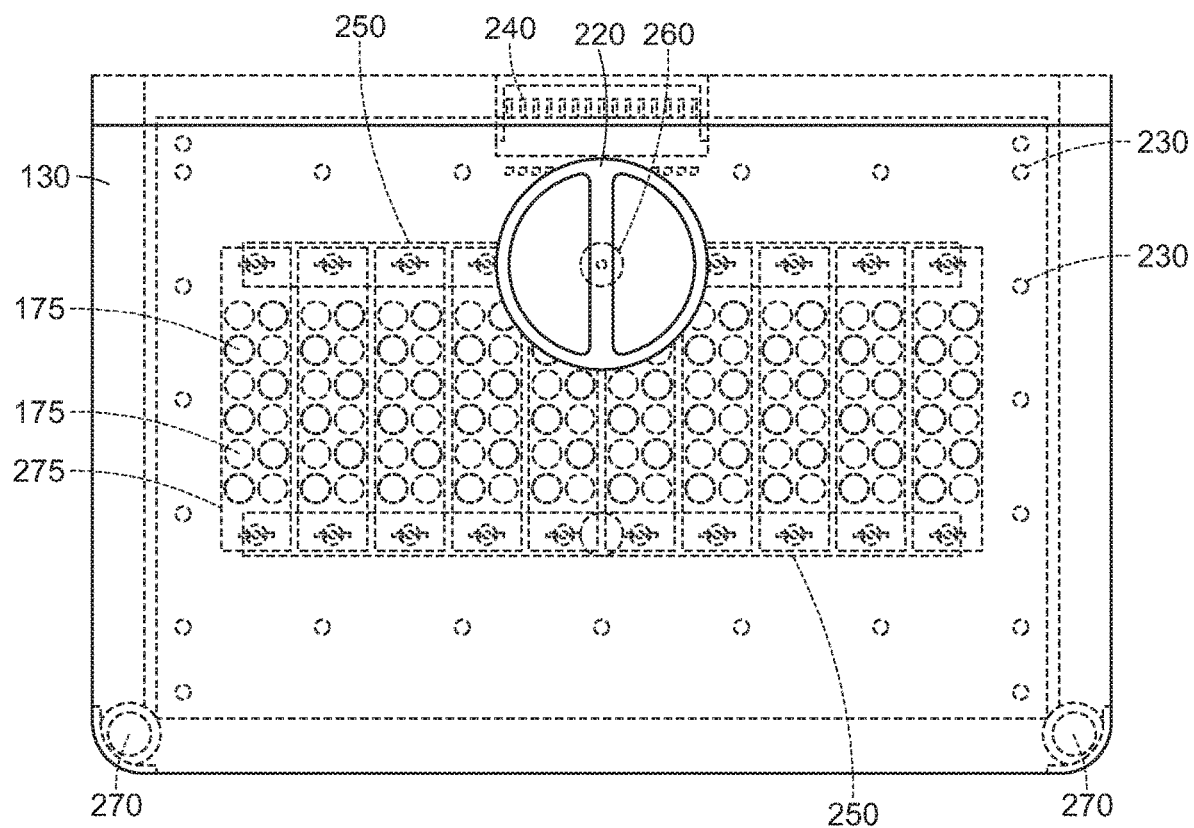
FIG. 12B is a plan view of another embodiment of the present invention configured to receive a centered or central oriented digit or group of digits.
Figure 12C:
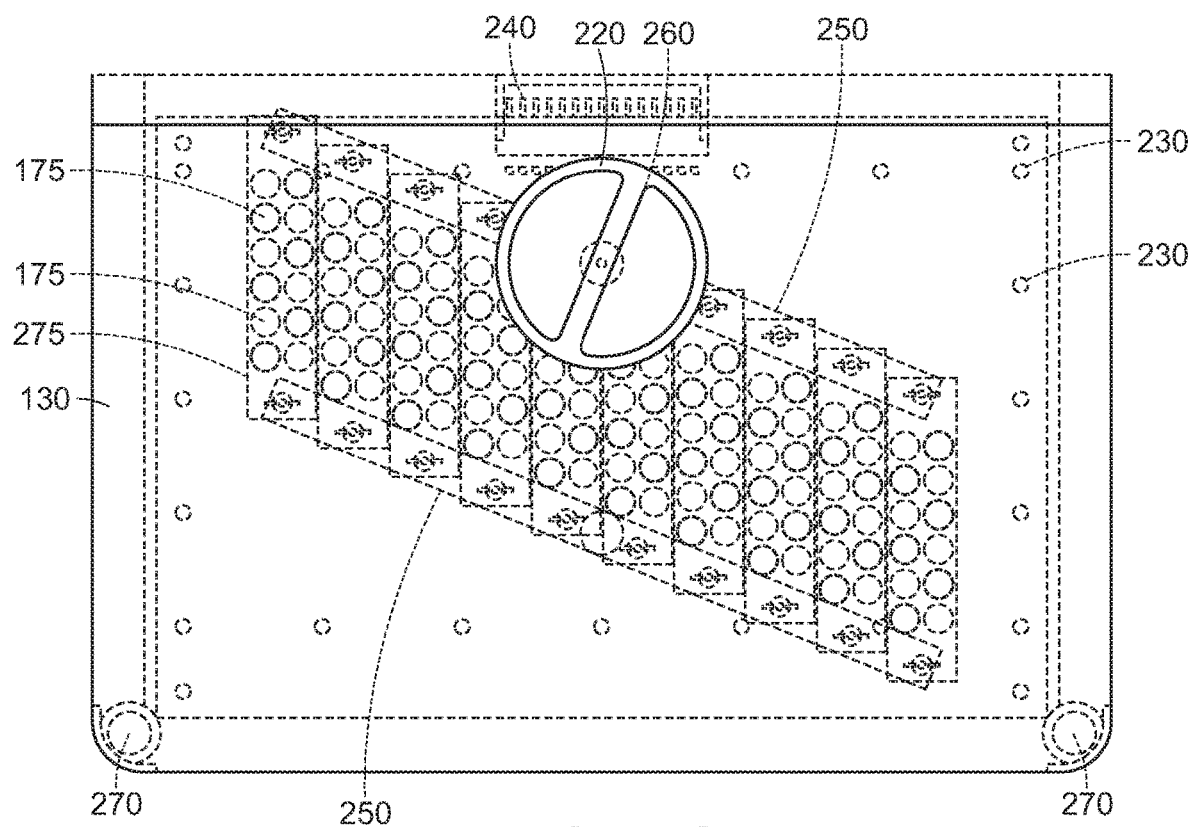
FIG. 12C is a plan view of another embodiment of the present invention configured to receive a right oriented digit or group of digits.

FIGS. 12A-C demonstrate another potential embodiment of the present invention. Shown is a plan view of an embodiment of the device 100 having a hinged and/or removable lid 130 being supported by at least two support posts 270 and being coupled via a male connector 240 to a compatible female connector preferably residing on the device body. On an underside of the lid 130 is a plurality of LEDs 175 arranged in an array 275. The plurality of LEDs 175 are preferably consistent in operative wavelength as previously described herein, however, other wavelengths or combinations of wavelengths may be contemplated. The array 275 is bound along at least one lateral edge, preferably two edges, by rotatable bars 250 which enable the rotation of the array 275 as a whole, thus causing the LEDs to rotate in unison along a fixed path. Further, along an underside of the lid 130 are a plurality of UV LEDs 230 embedded and/or protruding therefrom. The UV LEDs 230 preferably do not form part of the array 275 and may not be present in some embodiments.

On an outer surface of the lid 130 there is a dial 220 coupled to the array 275 via a rotatable mechanism 260. The dial 220 is configured to freely rotate between at least three different positions as shown in each of FIGS. 12A, B, and C. The dial 220, when rotated, causes rotation of the rotatable mechanism 260 which, in turn, causes rotation of the arrangement or orientation of the array 275 as a whole.

The rotation of the array 275 provides a number of advantages. For example, by manipulating the dial 220 one can more closely align the array 275 with the particular angle formed by the foot or other appendage of the user. This enables comprehensive coverage of all digits for both the left and the right foot. Thus, a user may desire to treat their left foot (see FIG. 12A) and then orient the array 275 to treat their right foot (see FIG. 12C). Each of the orientations ensures that all digits receive an overlapping treatment of light and does not require the appendage or digit to be inserted at an awkward or uncomfortable angle. In other more neutral arrangements that relate potentially to the hands or individual digits a central or neutral position may be desired (see FIG. 12B). If one were to not have the flexibility to orient the array 275 to fit their appendages angle, then the appendage itself must be oriented at potentially uncomfortable angles and may be further constrained by the construction of the device itself.

Figure 13A:
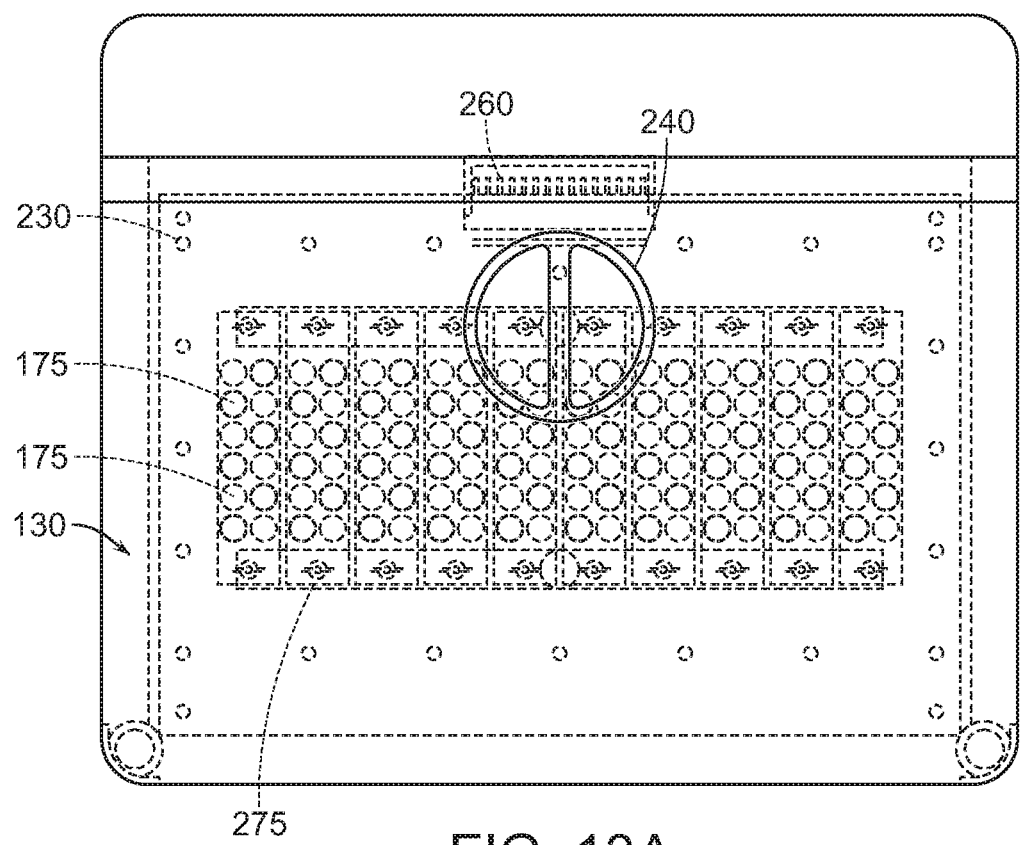
FIG. 13A is a top view of an embodiment of the present invention.
Figure 13B:
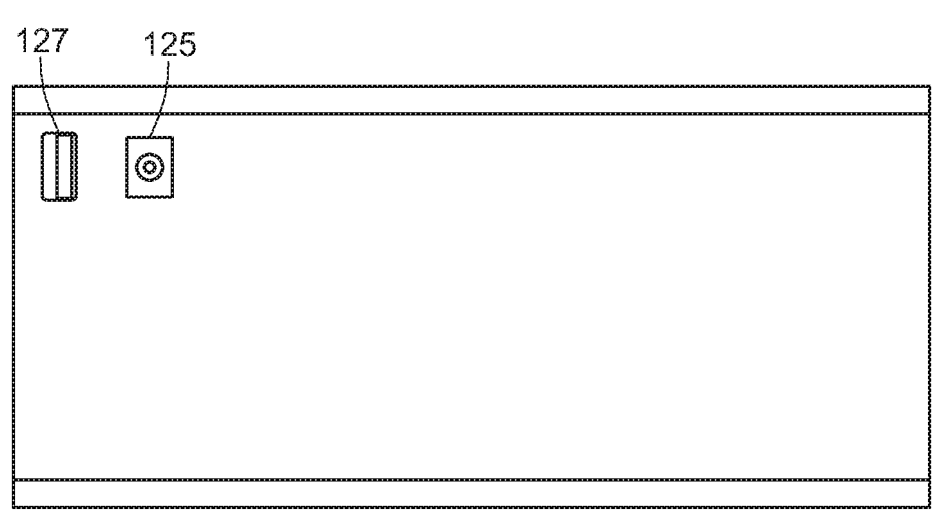
FIG. 13B is a back view of an embodiment of the present invention.
Figure 13C:
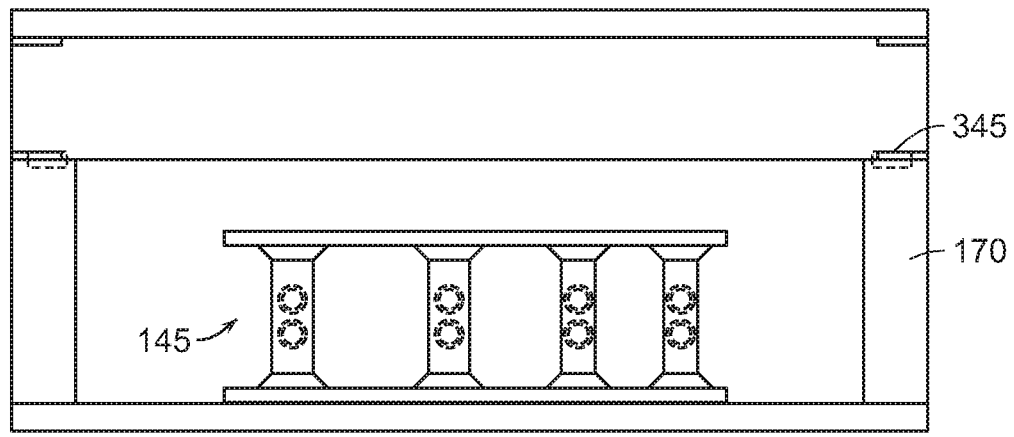
FIG. 13C is a front view of an embodiment of the present invention.

Referring now to FIGS. 13A-D there are varying views of an embodiment of the present invention. The views show the device 100 from the top (FIG. 13A), the front (FIG. 13C), the side (FIG. 13D), and the back (FIG. 13B).

In FIG. 13A, there is a top view of the device. The top of the device has a dial 260 that enables rotation of the light array 275 contained on an underside of the lid 130. The lid 130 is supported by the remaining device structure, as well as the support posts 170. The support posts 170 have a coupling mechanism 345 such as a high strength (ex. Neodymium) magnet to secure the position of the lid 130 while the device is in use.

The light array 275 is rotatably coupled to the lid 130. The dial 260 enables the light array to be directed to conform to an orientation desired by the user. The array 275 is flanked by a plurality of UV LEDs 230 which are embedded or protrude from the underside of the lid surface. The light array 275, in contrast, has lights that emit wavelengths consist with those previously described herein. In some instances, as further described below, the lid 130 may be removed to allow for a differing array with a differing set of LEDs to be coupled to the device body.

As seen from the front, the support posts 170 define an "open concept" that allows a digit(s) or appendage to be freely inserted into the digit/appendage receiving area 145. This non-restrictive opening allows the user to adjust the orientation of their digit/appendage while also providing for adequate airflow to help dissipate any residual heat generated by the LEDs. Further, the open concept is shown from the side in FIG. 13D. Thus, the digit receiving area 145 is substantially open, albeit for the support posts 170, along three sides of the device. The remaining closed side is preferably the back side of the device.

Figure 13D:
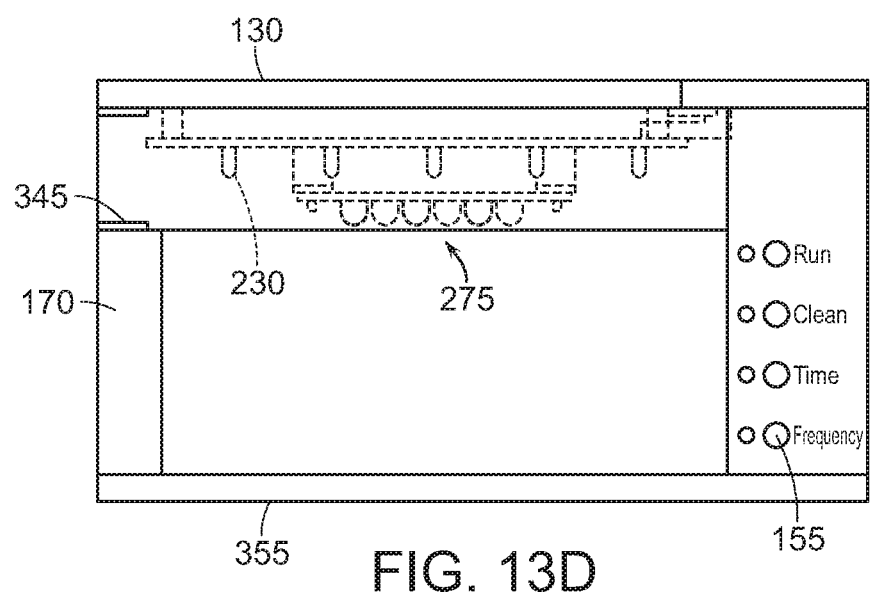
FIG. 13D is a side view of an embodiment of the present invention.

Also shown in FIG. 13D, are the status LEDs 155. There may be any number of operational statuses as described herein or otherwise contained under the purview of the present invention. For example, the status LEDs shown in FIG. 13D correspond to a "run" cycle, a "clean" cycle, a "timed" cycle, and a "frequency" cycle. The cycles or settings shown on the device in use may be the same or different as reflected herein in the drawings.

Figure 15A:
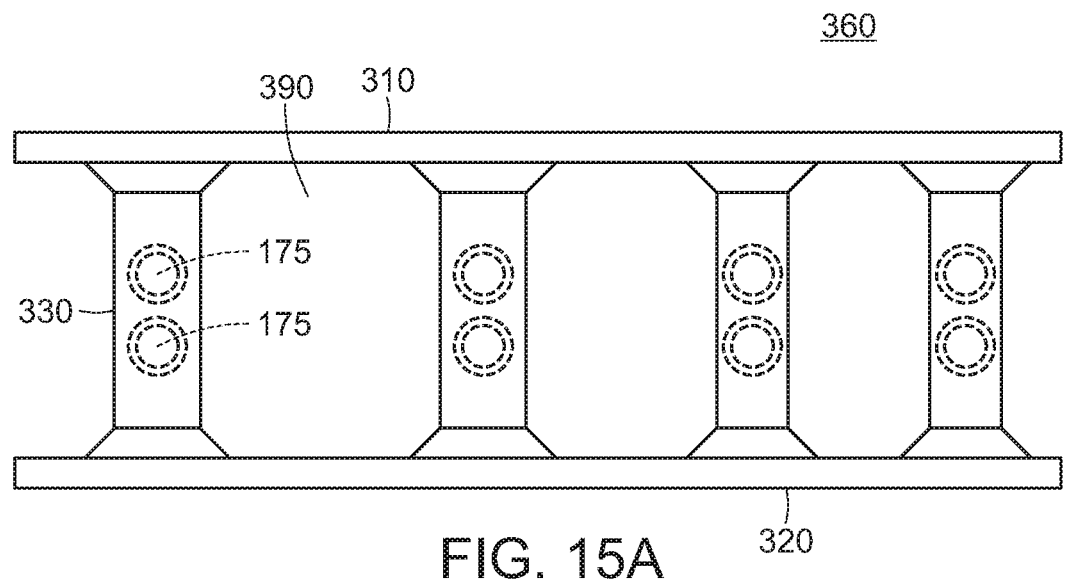
FIG. 15A is a side view of an embodiment of a digit spacing apparatus.
Figure 15B:
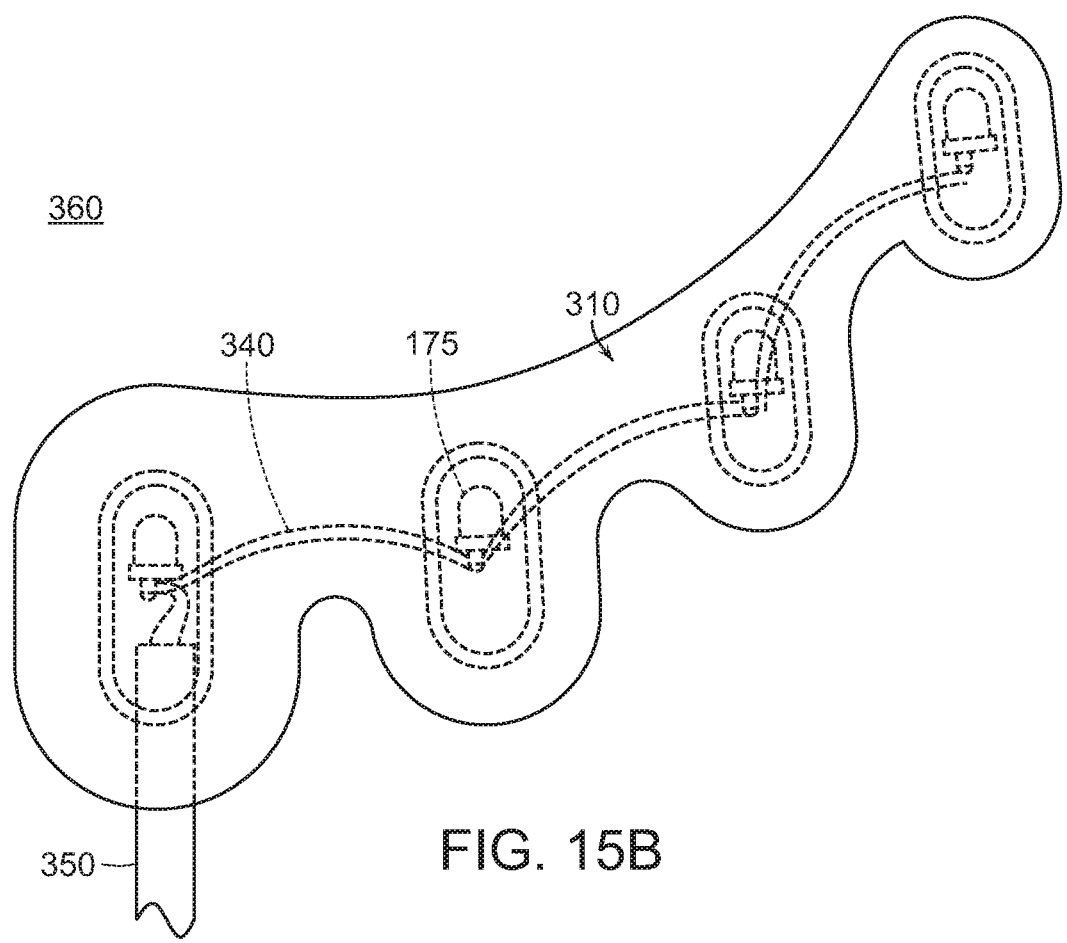
FIG. 15B is a top view of an embodiment of a digit spacing apparatus.
Figure 16:
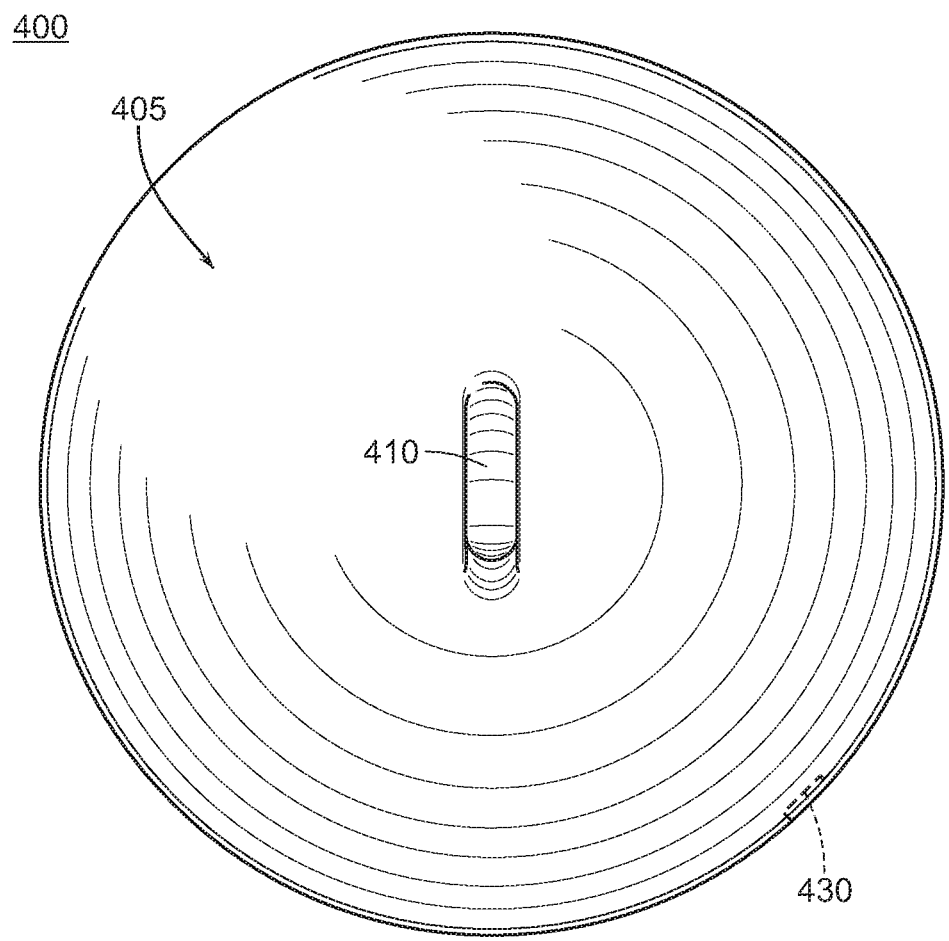
FIG. 16 is a top view of another embodiment of the present invention.
Figure 17:
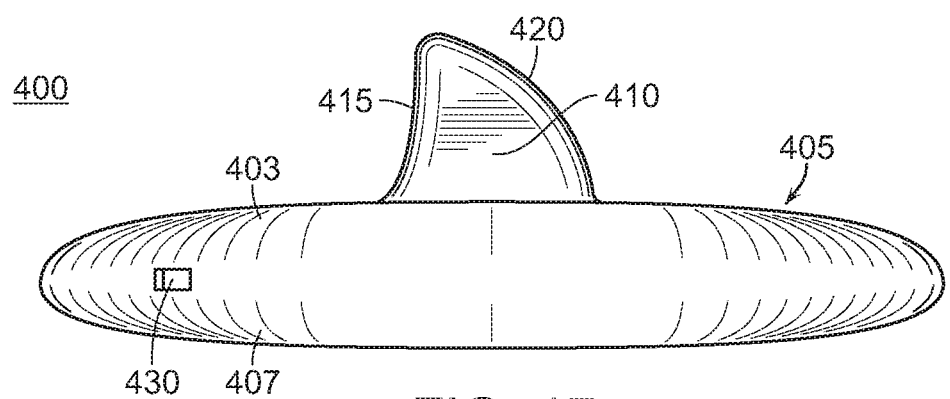
FIG. 17 is a side view of another embodiment of the present invention.
Figure 18:
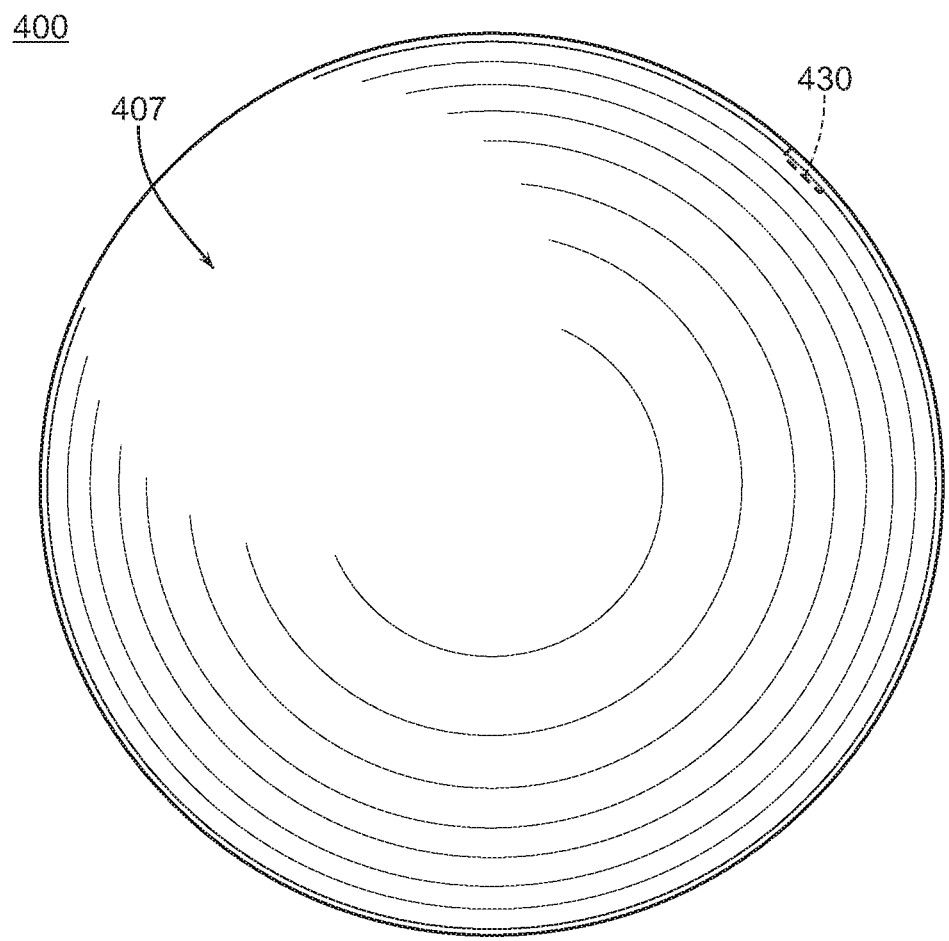
FIG. 18 is a bottom view of another embodiment of the present invention.
Figure 19:
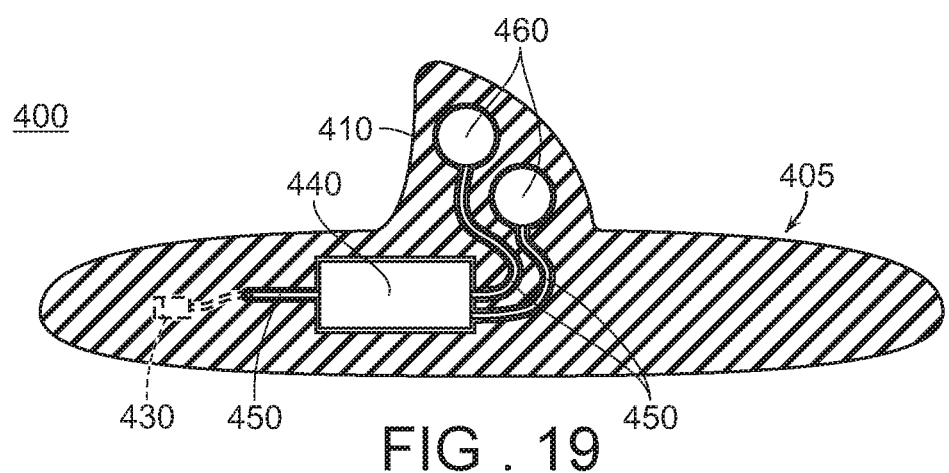
FIG. 19 is a cross-sectional side view of another embodiment of the present invention.

The backside of the device may contain a power input 125 as well as a power out 127. The power input 125 allows for connection of the power source 110 (see FIG. 2). The power out 127 may provide for a USB or other appropriate connection to supply electrical power to the digital spacing mechanism 360 as shown in FIGS. 15A-B.

Figure 14:
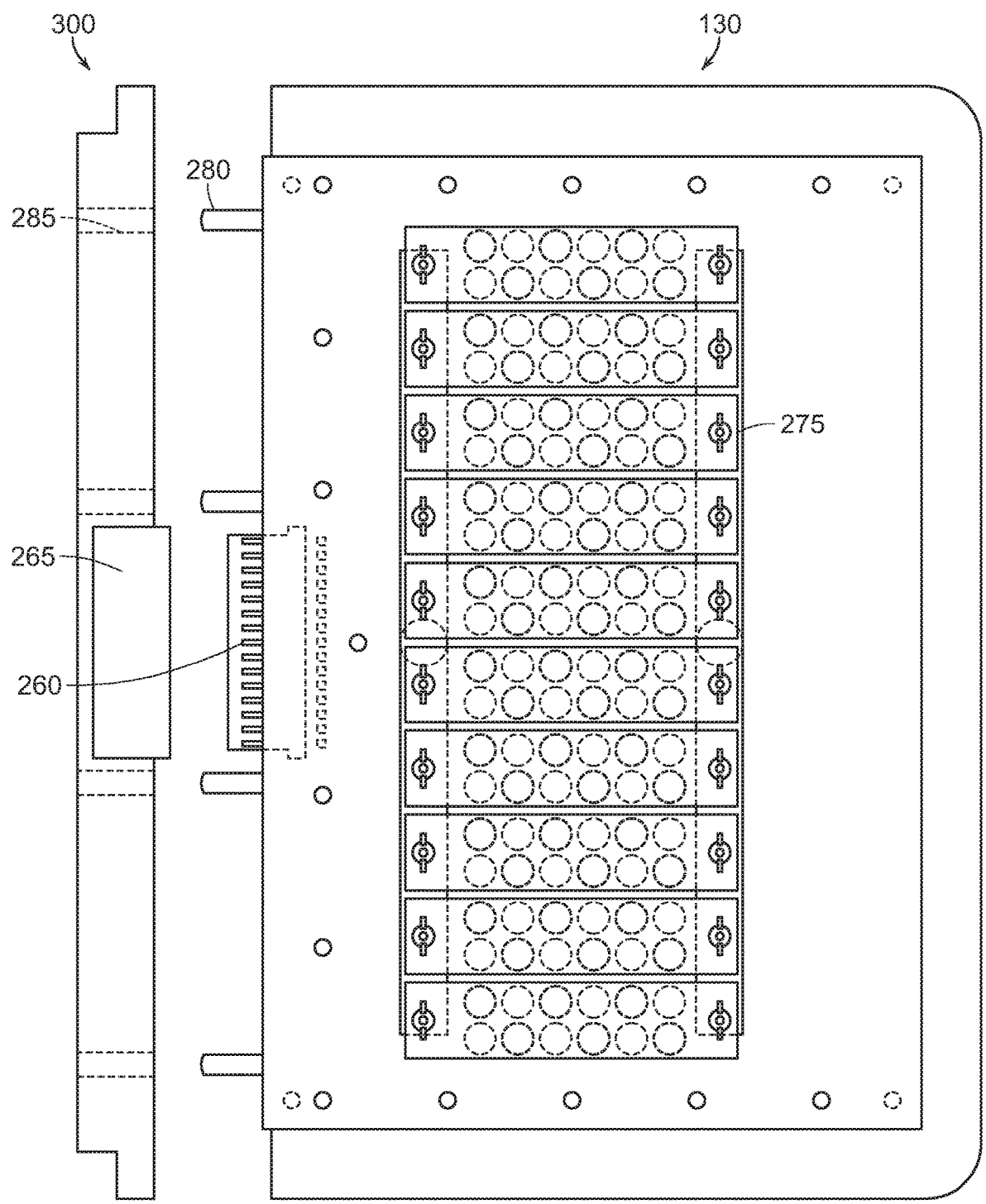
FIG. 14 is a front view of the lid raised and being detached from the remainder of the device body.

In FIG. 14, the lid 130, as described in FIG. 13A, may be detachable. The purpose of such a detachable lid 130 may provide for further cleaning of the device as well as provide for the changing and/or replacement of parts. For example, the lid 130 as shown is coupled to the female connector 265 which may be a Molex or other suitable style of connection. The male connector 240 fits within and is received by the female connector 265. As the male/female connectors are guided into place, the securement pins 280 are also secured to the device body.

The securement pins 280 provide rigidity to the lid 130 during use and prevent the lid 130 from being torqued in any one direction thereby preventing harm to the lid 130 or the connectors during use, storage, transport, and the like. The securement mechanisms 280 may be stainless steel or other metal, plastic, rubber, and the like dowels that are configured to fit into a receptacle 285. Each securement mechanism 280 is designed to fit into one receptacle 285 and in some embodiments multiple securement mechanisms may reside within a single receptacle.

In practice, the lid 130 may be removed in order to enable the array 275 to be changed for a different, yet similar array 275. For example, in order to offer treatments for different skin types it may be advantageous to have the device 100 have such a customization feature. Darker skin tones, having a higher concentration of melanin than lighter skin tones, will cause an increase in light absorption thereby detrimentally affecting the degree of penetration of the applied treatment. By changing out the lid 130 and subsequently the array 275 for another more suitable array 275 and associated wavelengths of light, it would enable proper treatment without the need for changing individual LEDs.

Referring now to FIGS. 15A-B, there is a digit spacing mechanism 360 capable of being used with embodiments of the present invention described herein. In some instances, the digit spacing mechanism 360 may be used without the need for the device 100 itself. The digit spacing mechanism 360 generally has a first surface 310, a second surface 320, at least two spacers 330 with LEDs 175 contained within the spacers 330. Further, a power in cable 350 and wiring 340 enable electronic communication between the device and the LEDs 175.

The digit spacing mechanism 360 may be comprised of any number of materials including but not limited to plastics, rubbers, foams, and silicone or any combination thereof. The first surface 310, second surface 320, and spacers 330 may each be comprised of the same or a different material. In order to permit the correct transmission of light during treatment (treatment to be delivered into the space between the digits) it is important that the material selected exhibits good optical clarity that enables transmission of light in all visible wavelengths and extending towards at least 500 nm on either side of the visible spectrum.

Preferably the first surface 310 and second surface 320 are positioned generally in a parallel fashion with regard to one another. The spacers 330 a preferably positioned there between and being coupled to each of the first surface 310 and the second surface 320. There is an interstitial space 390 between each of the spacers 330. Preferably, at least one and more preferably at least two LEDs 175 are disposed within each of the spacers 330. When two LEDs 175 are used, the LEDs emit light at about 870nm and about 940 nm, respectively.

The LEDs 175 are coupled via wiring 340 in a series connection with the wiring 340 embedded in preferably either the first surface 310 or the second surface 320. Further, the electrical power for operation of the digital spacing mechanism 360 is supplied via a power in cable 350. The power in cable 350 may be coupled to the device or the power source 110 (see FIG. 2).

The digit spacing mechanism 360 is intended to be ambidextrous in that a user may only need one of the mechanisms rather than two. In use, the digit spacing mechanism 360 can be fitted along, for example, a right foot, a left foot, a left hand, or a right hand. If used for one side (i.e. left side) to be used for the corresponding appendage on the right side of the body the mechanism must simply be inverted. Thus, the first surface 310 would reside on the bottom and the second surface 320 reside on the top when compared to the view shown in FIG. 15A. Further, the mechanism can be placed on the appendage before it is placed into the device for treatment.

Referring now to FIGS. 16-19, there is a device 400 having a body 405 and a protrusion 410. Further components may include a port 430, top 430, bottom 407, concave surface 415 convex surface 420, light source 460, power source 440, and wiring 450.

Generally, the device 400 has a top 430 and a bottom 407. The bottom 407 is generally planar or flat allowing the device 400 to be positioned on a surface. The device 400 may also be pliable to some degree allowing the bottom 407 to conform to an irregular surface. The top 403 is slightly rounded (convex) or in some embodiments may also be planar or flat.

From the middle area of the top 403, there is a protrusion 410. The protrusion 410 is configured to have a convex surface 420 and a concave surface 415. Within the protrusion 410 there is at least one light source 460. In some embodiments, there may be multiple light sources 460. The light sources 460 are configured to emit light having a wavelength of about 870 nm to about 930 nm. In some embodiments, the light source 460 may further be dispersed throughout the body 405.

A power source 440 may empower the light source(s) 460. In some embodiments, port 430 may be utilized to recharge the power source 440. In yet other embodiments, there is no self-contained power source and the port 430 utilizes a DC connection to a power outlet to provide operational electricity to the device 400.

The device 400 may be comprised of a silicone based material that allows for transmission of desired wavelengths of light. In use, a user would position the area between the toes or fingers against the protrusion 410 and activate the device 400 for the prescribed treatment time. Further, the device 400 may be comprised of materials that provide for a non-slip surface on at least a bottom 407 of the device 400. Further, the body 405 and protrusion 410 may be wholly comprised of a non-slip surface. An adhesive may also be disposed on the bottom 407 to prevent slippage of the device 400 while in use.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A method of treating a fungal infection comprising:
applying an effective amount of near infrared (NIR) light emitted from one or more NIR light emitting diodes (LEDs) from a device to a treatment area having the fungal infection of onychomycosis or tinea pedis for a first amount of time, said NIR light applied to said treatment site at an energy or power level sufficient to alleviate or treat the fungal infection of onychomycosis or tinea pedis and prevent thermal damage to said treatment site being exposed to said NIR LED light, wherein said NIR light emitting diodes comprise pairs of light emitting diodes with peak wavelengths of 870 nm and 930 nm, viewing angles of ±10°, average powers of 50 mW and 35 mW, and peak powers of 500 mW and 350 mW, respectively for each wavelength.

2. The method of treating a fungal infection according to claim 1, wherein said treatment area is exposed to NIR light for at least a second amount of time.

* * * * *